United States Patent [19]

Dubas

[11] Patent Number: 4,959,167

[45] Date of Patent: Sep. 25, 1990

[54] ASYMMETRIC DISULFIDES IN LUBRICANT COMPOSITIONS

[75] Inventor: Henri Dubas, Marly, Switzerland

[73] Assignee: Ciba-Geigy Corporation, Ardsley, N.Y.

[21] Appl. No.: 305,834

[22] Filed: Feb. 2, 1989

[30] Foreign Application Priority Data

Feb. 12, 1988 [CH] Switzerland .................. 516/88-8

[51] Int. Cl.$^5$ .................................. C10M 135/20
[52] U.S. Cl. ........................... 252/32.7 E; 252/32.5; 252/32.7 R
[58] Field of Search .............. 252/32.7 E, 47, 32.5, 252/32.7 R, 47.5

[56] References Cited

U.S. PATENT DOCUMENTS

| | | | |
|---|---|---|---|
| 3,523,897 | 8/1970 | De Vault | 252/32.7 E |
| 3,544,531 | 12/1970 | Morita et al. | 260/79.5 |
| 3,687,848 | 8/1972 | Colclough | 252/32.7 E |
| 3,742,099 | 6/1973 | Colclough | 252/32.7 E |
| 3,769,211 | 10/1973 | Collen | 252/32.7 E |
| 4,482,463 | 11/1984 | Dubas et al. | 252/47.5 |

FOREIGN PATENT DOCUMENTS

0166696  5/1985  European Pat. Off. .

OTHER PUBLICATIONS

B. A. Khaskin, Zhurnal Obshchei Khimii, 50(12), pp. 2700-2703.
C. A. 94(12), #95076.

*Primary Examiner*—Olik Chaudhuri
*Assistant Examiner*—James M. Hunter, Jr.
*Attorney, Agent, or Firm*—Stephen V. O'Brien

[57] ABSTRACT

Lubricant compositions or hydraulic fluid compositions containing
(a) at least one lubricant or one hydraulic fluid and
(b) at least one compound of the formula

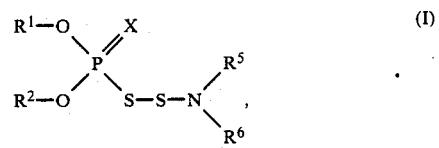

in which $R^1$ and $R^2$ are identical or different and are each an alkyl group having 1 to 30 C atoms, an unsubstituted or $C_1$–$C_8$alkyl-substituted cycloalkyl group having 5 to 12 C atoms or an unsubstituted or $C_1$–$C_{12}$-alkyl-substituted $C_6$–$C_{10}$aryl group, or $R^1$ and $R^2$ together are an unsubstituted or $C_1$–$C_{12}$alkyl-substituted alkylene group haivng 2 to 20 C atoms or an arylene group having 6 to 20 C atoms, and $R^5$ and $R^6$ are identical or different and are each an alkyl group having 1 to 30 C atoms, or $R^5$ and $R^6$ together are an unsubstituted or $C_1$–$C_{12}$alkyl-substituted alkylene group having 2 to 20 C atoms or an alkylene group which has 2 to 10 C atoms and is interrupted by —O—, —S— or —NR$^9$—, in which R$^9$ is H or $C_1$–$C_4$alkyl, and X is O or S.

15 Claims, No Drawings

ASYMMETRIC DISULFIDES IN LUBRICANT COMPOSITIONS

The invention relates to compositions containing asymmetric disulfides, and to novel asymmetric disulfides and novel preparation processes, and to the use of the asymmetic disulfides in lubricant compositions or hydraulic fluid compositions.

Various additives are in general added to mineral oils and synthetic or semi-synthetic lubricants and also hydraulic fluids in order to improve their use properties. In particular, there is a need for additives which are intended to protect the devices to be lubricated from frictional wear. Such wear inhibitors are required to increase the load-bearing capacity of the lubricant and not to have a corrosive effect on the metal components to be protected.

Various phosphorus compounds, especially compounds of the zinc dialkyl dithiophosphate series, are thus used today as high pressure and antiwear additives. Metal- and especially zinc-containing compounds are undesirable in engine oil in connection with the efficiency of exhaust purification catalysts in the exhaust systems of petrol engines, since their constituents, which may enter the catalyst, impair the activity of this. Such zinc-free additives have already been described, for example, in EP-A 0,166,696.

Lubricating oil formulations which contain a mixture of phosphorus thionyl- or phosphorus sulfide and ammonium thiophosphate as an additive have moreover been disclosed in DE-A 2,031,505.

The use of polysulfides containing 2 N atoms as lubricant additives is known from EP-A 0,076,784.

The high pressure and antiwear properties of lubricants containing such additives are often not satisfactory. In particular, the heat stability may be inadequate, and corrosion may occur to copper and iron. Some alkylaminodialkoxyphosphinothionyl disulfides have furthermore been disclosed in B.A. Khaskin, N.A. Tolmacheva and V.K. Promonenkov, Zhurnal Obshchei Khimii, volume 50, No. 12, pages 2700–2703, December 1980.

Compositions and compounds which have a very good high pressure and antiwear action, exhibit reduced corrosiveness, also to copper, and contain no zinc have now been found.

The lubricant compositions or hydraulic fluid compositions according to the invention contain
(a) at least one lubricant or one hydraulic fluid and
(b) at least one compound of the formula

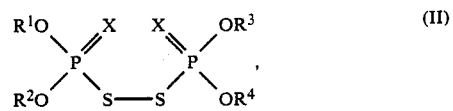

in which $R^1$ and $R^2$ are identical or different and are each an alkyl group having 1 to 30 C atoms, an unsubstituted or $C_1$–$C_8$-alkyl-substituted cycloalkyl group having 5 to 12 C atoms or an unsubstituted or $C_1$–$C_{12}$-alkyl-substituted $C_6$–$C_{10}$-aryl group, or $R^1$ and $R^2$ together are an alkylene group having 2 to 20 C atoms or an arylene group having 6 to 20 C atoms, and $R^5$ and $R^6$ are identical or different and are each an alkyl group having 1 to 30 C atoms, or $R^5$ and $R^6$ together are an unsubstituted or $C_1$–$C_{12}$-alkyl-substituted alkylene group having 2 to 10 C atoms or an alkylene group which has 2 to 10 C atoms and is interrupted by —O—, —S— or —$NR^9$—, in which $R^9$ is H or $C_1$–$C_4$-alkyl, and X is O or S.

The compounds of the formula (I) can be added to the lubricant or hydraulic fluid as such. However, they can also be produced in this in situ. Lubricant compositions or hydraulic fluid compositions containing a compound of the formula (I) formed in situ in the lubricant or in the hydraulic fluid as a reaction product of at least one compound of the formula

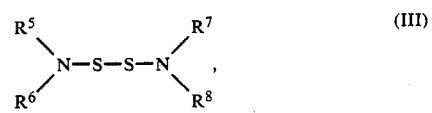

in which $R^1$ and $R^2$ are as defined above and $R^3$ and $R^4$ are identical or different and are as defined above for $R^1$ or $R^2$, or $R^3$ and $R^4$ together are as defined for $R^1$ and $R^2$ together, and at least one compound of the formula $$\begin{array}{c} R^5 \\ \diagdown \\ R^6 \diagup \end{array} N-S-S-N \begin{array}{c} \diagup R^7 \\ \diagdown R^8 \end{array} \quad (III)$$

in which $R_5$ and $R^6$ are as defined above and $R^7$ and $R^8$ are identical or different and are as defined above for $R^5$ or $R^6$, or $R^7$ and $R^8$ together are as defined above for $R^5$ and $R^6$ together, are therefore to be mentioned in particular.

Compounds of the formula (II) in which in each case $R^1$ is identical to $R^2$ and $R^3$ is identical to $R^4$ have proved advantageous. Compounds of the formula (III) in which in each case $R^5$ is identical to $R^6$ and $R^7$ is identical to $R^8$ are advantageous. Compounds of the formula (II) in which in each case all four substituents are identical, $R^1$, $R^2$, $R^3$ and $R^4$ being as defined, are particularly advantageous. Compounds of the formula (III) in which in each case all four substituents are identical and $R^5$, $R^6$, $R^7$ and $R^8$ are as defined have also proved to be particularly advantageous.

The substituents $R^1$ to $R^8$ can thus independently of one another be, for example, a straight-chain or branched alkyl group, advantageously having 1–30 carbon atoms.

Examples of these are methyl, ethyl, n-propyl, isopropyl, n-butyl, sec-butyl, t-butyl, isoamyl, n-hexyl, 2-ethylbutyl, pentyl, 1-methylpentyl, 1,3-dimethylbutyl, 1,1,3,3-tetramethylbutyl, 1-methylhexyl, isoheptyl, n-octyl, 2-ethylhexyl, 1-methylheptyl, 1,1,3-trimethylhexyl, n-decyl, 1-methylundecyl or n-dodecyl, tetradecyl, hexadecyl, octadecyl and eicosyl. 2-Ethylhexyl is preferred, 2-ethylhexyl being of great practical interest for $R^5$ and $R^6$.

Examples of an unsubstituted or $C_1$–$C_8$-alkyl-substituted cycloalkyl group having 5–12 C atoms which can be used for the substituents $R^1$ to $R^4$ are cyclopentyl, cyclohexyl, 2-methylcyclohexyl, 4-methylcyclohexyl, di-methylcyclohexyl, trimethylcyclohexyl, t-butylcyclohexyl, cycloheptyl, cyclooctyl and cyclododecyl. The cyclohexyl group is preferred.

An unsubstituted or $C_1$–$C_{12}$-alkyl-substituted $C_6$–$C_{10}$-aryl group $R^1$ to $R^4$ can be, for example, phenyl, methyl-phenyl, dimethylphenyl, trimethylphenyl, ethylphenyl, diethylphenyl, isopropylphenyl, tert-butylphenyl, di-tertbutylphenyl or 2,6-di-tert-butyl-4-methylphenyl. The phenyl group is preferred.

$R^1$ and $R^2$ together and/or $R^3$ and $R^4$ together, and $R^5$ and $R^6$ together and/or $R^7$ and $R^8$ together can be an alkylene group having 2 to 20 C atoms, or, respectively, 2-10 C atoms, which is unsubstituted or substituted by alkyl having a total of 1 to 12 C atoms. Examples of these groups are ethylene, propylene, trimethylene, tetramethylene, pentamethylene, hexamethylene, octamethylene, decamethylene and dodecamethylene, and furthermore 2-methyl-2-n-propyltrimethylene, 2-methyl-2-n-butyl-trimethylene, 1,1-dimethyl-2,2-dimethyldimethylene, 1,1,2-trimethyl-2-n-propyltrimethylene, 2-ethyl-2n-butyltrimethylene, 1-isopropyl-2,2-dimethyltrimethylene, 1-methyltrimethylene, 2,2-dimethyltrimethylene, 1,1,3-trimethyltrimethylene and 2,2,4- or 2,4,4-trimethylhexamethylene. The trimethylenes, and amongst these 2-methyl-2-n-propyl or 2-methyl-2-n-butyltrimethylene or 1-iso-propyl-2,2-dimethyltrimethylene, for $R^1$ and $R^2$, are of particular importance.

As arylene having 6 to 20 C atoms, $R^1$ and $R^2$ together and/or $R^3$ and $R^4$ together can be, for example, 1,2-phenylene, 1,3-phenylene or 1,4-phenylene. $R^5$ and $R^6$ together and/or $R^7$ and $R^8$ together can in each case form an alkylene group which has 2 to 10 C atoms and is interrupted by —O—, —S— or —NR$^9$—, in which $R^9$ is H or $C_1$-$C_4$-alkyl. The groups of the formulae —(CH$_2$)$_2$—O—(CH$_2$)$_2$— and

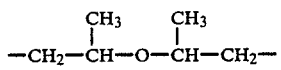

are preferred.

Compounds in which $R^5$ and $R^6$ together with the N atom linking them are a morpholino group are also of great practical interest.

Compounds of the formulae (I) and (II) in which the substituents $R^1$ and $R^2$ are identical and are each an alkyl group having 5 to 12 C atoms, phenyl, a $C_1$-$C_8$-alkyl-substituted phenyl group or an unsubstituted or $C_1$-$C_4$-alkyl-substituted cycloalkyl group having 6-8 C atoms, or $R^1$ and $R^2$ together are a branched alkylene group having 4-9 C atoms are preferred.

Other preferred compounds of the formulae (I) and (III) include those in which the substituents $R^5$ and $R^6$ are identical and are preferably an alkyl group having 5-12 C atoms, or $R^5$ and $R^6$ together are an alkylene group having 4 to 6 C atoms or an alkylene group which has 4 to 6 C atoms and is interrupted by —O—, and preferably —(CH$_2$)$_2$—O—(CH$_2$)$_2$— or

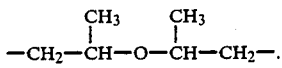

The preferred embodiments furthermore include compounds of the formula (I) and (II) in which X is S.

The compounds of the formula (I) according to the invention can be prepared by various processes, which are known per se, for asymmetric disulfides.

A preparation process which is suitable per se can be found in the abovementioned literature reference of B.A. Kashin, N.A. Tolmacheva and V.K. Promonenkov, Zhurnal Obshchei Khimii, volume 50, No. 12, pages 2700–2703, December 1980. This process follows the equation shown below in general form:

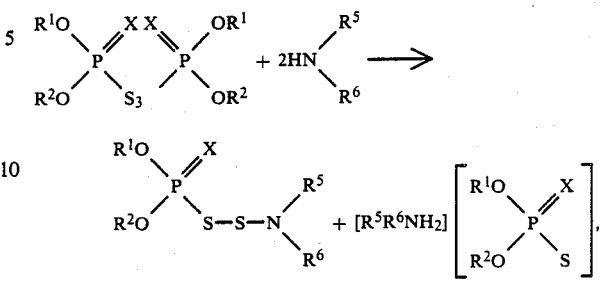

in which, in this case, $R^1$, $R^2$, $R^5$, $R^6$ and X can be as defined above.

Another suitable preparation process is halogenation, and in particular bromination, of a secondary diaminodisulfide and subsequent reaction of the amidosulfenyl halide, or, respectively, amidosulfenyl bromide, generated in situ, with an alkali metal dithiophosphate.

The compounds of the formula (I) can also be prepared, for example, by reaction of compounds of the formulae (II) and (III), the formulae (II) and (III) being as defined above. The process can be carried out in a solvent, for example toluene, by boiling under reflux at about 110° C. for about 10 to 20 hours. The solvent can then be removed and the reaction mixture can be further used as such. The compounds of the formula (I) can also be isolated from the reaction mixture and then further used.

The compositions according to the present invention can accordingly be prepared by mixing the compounds of the formula (II) and of the formula (III) and admixing the reaction mixture or the compounds of the formula (I) isolated from the reaction mixture with a lubricant or a hydraulic fluid.

The lubricant composition or hydraulic fluid composition according to the invention can be obtained by addition of an active amount, advantageously 0.01 to 10% by weight, preferably 0.1 to 5 and especially preferably 0.5 to 2% by weight, based on the composition, of one or more compounds of the formula (I) to a lubricant or to a hydraulic fluid.

The present invention also relates to a process for the preparation of a lubricant composition or hydraulic fluid composition containing at least one compound of the formula (I) by adding at least one compound of the formula (II) and at least one compound of the formula (III) to the lubricant or the hydraulic fluid and mixing all the components, the compounds of the formula (II) and of the formula (III) advantageously being admixed in a combined concentration of 0.01 to 10% by weight, based on the composition.

The compounds of the formulae (II) and (III) can be used, that is to say mixed together, in an equimolar amount or also in an amount which deviates somewhat from the strictly mathematical equimolar ratio. It is moreover possible to aim for an equimolar mixture, and in addition in order to achieve or intensify other desirable properties of the end product, it is possible to add certain amounts either of the compound of the formula (II) or of the compound of the formula (III), that is to say in a mathematical excess.

The lubricant compositions or hydraulic fluid compositions according to the invention therefore also include those containing the compounds of the formula (I) and the remaining compounds of the formulae (II) and/or (III) where the compounds of the formulae (II) and (III) are used in molar mixing ratios of, for example, 3:1 to 1:3, advantageously of 3:2 to 2:3 and preferably of 5:4 to 4:5.

The invention can accordingly also include lubricant compositions or hydraulic fluid compositions which also contain compounds of the formula (II) and/or (III) in addition to compounds of the formula (I).

All the preparation processes which start from compounds of the formula (II) and (III) have the common feature that the mixtures of the compounds of the formula (II) and of the formula (III), or the lubricant or the hydraulic fluid containing the compounds of the formulae (II) and (III) are advantageously exposed to a temperature of 25° to 150° C., preferably 60° to 120° C. and especially preferably 100° to 120° C., so that the compounds of the formula (I) are formed in the maximum possible yield.

To prepare a lubricant composition or hydraulic fluid composition containing a compound of the formula (I), a process is preferred which comprises mixing an equimolar amount of a compound of the formula

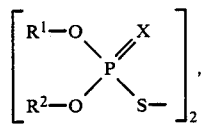

(IV)

in which $R^1$, $R^2$ and X are as defined above, with a compound of the formula

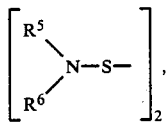

(V)

in which $R^5$ and $R^6$ are as defined above.

The compounds of the formula (II) and thus of the formula (IV) are known and are accessible, for example, by oxidation of dialkyl-dithiophosphoric acid with sodium hypochlorite (US-A 3,885,001). The compounds of the formula (III) and thus of the formula (V) are likewise known and are obtained by reaction of dialkylamines with disulfur dichloride in the presence of sodium hydroxide (EP-A 76,784). Another preparation process for compounds of the formula (III) is known, for example, from DE-B 2,031,505.

The compounds of the formula (I) according to the invention are of a liquid or viscous to solid consistency. They are very readily soluble in non-polar organic substances (for example in lubricating oils).

An advantageous preparation process comprises admixing the compounds of the formulae (II) and (III) with a lubricant or a hydraulic fluid in amounts such that the compounds of the formula (I) and any excesses of compounds of the formula (II) or (III) together make up 0.01 to 99% by weight and preferably 10 to 50% by weight, based on the lubricant or the hydraulic fluid.

Such mixtures can then be further used directly or can be concentrates which are added in the desired amounts, shortly before use, to a lubricant to be improved or to a hydraulic fluid to be improved. The dilution of the additives according to the invention here should not fall below the concentration needed for an activity, that is to say the compound of the formula (I) or the sum of the compounds of the formulae (I), (II) and (III) in compositions according to the invention should preferably be at least 0.01% by weight of the ready-to-use lubricant or of the hydraulic fluid. Finally, as a rule, the ready-to-use lubricant or the hydraulic fluid should contain the compounds of the formulae (II) and/or (III) and the compounds of the formula (I) formed therefrom in combined amounts of 0.01 to 10% by weight, advantageously 0.1 to 5% by weight and preferably 0.5 to 2% by weight.

The compounds of the formula (I), if appropriate mixed with compounds of the formulae (II) and/or (III), are used, for example, as additives for lubricants, for example for engine oils. The lubricant can be an oil or grease based on a mineral oil or synthetic oil or mixtures thereof. This also includes mineral oils used for lubricating purposes and based on hydrocarbon compounds, and synthetic oils from the series comprising aliphatic or aromatic carboxylic esters, polymeric esters, polyalkylene oxides, phosphoric acid esters, poly-α-olefins and silicones. Greases can be obtained from these oils mixed with metal soaps or equivalent thickeners. Such compounds are described comprehensively in: "Schmiermittel Taschenbuch" (Lubricants Handbook) (Hüthig Verlag, Heidelberg, 1974), "Ullmanns Encyclopädie der technischen Chemie" (Ullmann's Encyclopedia of Industrial Chemistry), volume 13, pages 85–94 (Verlag Chemie, Weinheim, 1977) and D. Klamann, "Schmierstoffe und verwandte Produkte" (Lubricants and Related Products), pages 158–174 (Verlag Chemie, Weinheim, 1982).

The novel lubricant compositions have a high-pressure and antiwear action and corrosion-inhibiting action in lubricating systems. A particular advantage of the compounds of the formula (I) is that, in contrast to compounds having similar properties, they are free from zinc and tin and therefore free from ash, which means that after-burning of the exhaust gases in catalyzed systems is also not impaired. In addition, the compounds are low in phosphorus and are therefore less susceptible to the growth of microorganisms. Finally, less phosphate is obtained on disposal of the substances, which contributes towards avoiding the known environmental problems.

The reduction in the corrosion of copper should be mentioned in particular. It has been found, in particular, that the desired high-pressure and wear properties of both molecular parts in the asymmetric product of the formula (I) complement one another unexpectedly and surprisingly well and the response temperature is synergistically reduced, whereas the adverse secondary properties, such as the copper corrosiveness referred to and the high melting point of the starting substances of the formulae (II) and (III), largely disappear.

The compounds of the formula (I), if appropriate mixed with compounds of the formulae (II) and/or (III), can also be used in hydraulic fluids based on mineral and/or synthetic oils, which may contain variable amounts of water, in which case oil-in-water or water-in-oil emulsions can be the suitable use forms.

The lubricants and hydraulic fluids can additionally contain other additives which are added in order to improve the basic properties of lubricants or hydraulic fluids still further; these include: antioxidants, metal passivators, rust inhibitors, agents for improving the viscosity index, agents for lowering the pour point, dispersants, detergents and further high-pressure additives and antiwear additives. some examples of such additional additives are listed below:

EXAMPLES OF PHENOLIC ANTIOXIDANTS

1. Alkylated monophenols 2,6-Di-tert-butylphenol, 2,6-di-tert-butyl-4-methylphenol, 2,6-di-tert-butylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-iso-butylphenol, 2,6-di-cyclopentyl-4-methylphenol, 2-(α-methylcyclohexyl)-4,6-dimethylphenol, 2,6-di-octadecyl-4-methylphenol, 2,4,6-tri-cyclohexylphenol, 2,6-di-tert-butyl-4-methoxymethylphenol and o-tert-butylphenol.

2. Alkylated hydroquinones 2,6-Di-tert-butyl-4-methoxyphenol, 2,5-di-tert-butylhydroquinone, 2,5-di-tert-amyl-hydroquinone and 2,6-diphenyl-4-octadecyloxyphenol.

3. Hydroxylated thiodiphenyl ethers 2,2'-Thio-bis-(6-tert-butyl-4-methylphenol), 2,2'-thio-bis-(4-octylphenol), 4,4'-thio-bis-(6-tert-butyl-3-methylphenol) and 4,4'-thio-bis-(6-tert-butyl-2-methylphenol).

4. Alkylidene-bisphenols 2,2'-Methylene-bis-(6-tert-butyl-4-methylphenol), 2,2'-methylene-bis-(6-tert-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-iso-butylphenol), 2,2'-methylene-bis-[6-(α-methylbenzyl)-4-nonylphenol], 2,2'-methylene-bis[6-(α,α-dimethylbenzyl)-4-nonylphenol], 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)-butane, 2,6-di-(3-tert-butyl-5-methyl-2-hydroxybenzyl)-4-methylphenol, 1,1,3-tris-(5-tert-butyl-4-hydroxy-2-methylphenyl)-3-n-dodecylmercaptobutane, ethylene glycol bis-[3,3-bis-(3'-tert-butyl-4'-hydroxyphenyl)-butyrate], bis-(3-tert-butyl-4-hydroxy-5-methylphenyl)-dicyclopentadiene and bis-[2-(3'-tert-butyl-2'-hydroxy-5'-methyl-benzyl)-6-tert-butyl-4-methylphenyl]terephthalate.

5. Benzyl compounds 1,3,5-Tri-(3,5-di-tert-butyl-4-hydroxybenzyl)-2,4,6-trimethylbenzene, bis-(3,5-di-tert-butyl-4-hydroxybenzyl) sulfide, isooctyl 3,5-di-tert-butyl-4-hydroxybenzylmercaptoacetate, bis-(4-tert-butyl-3-hydroxy-2,6-dimethylbenzyl)-dithiol terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, dioctadecyl 3,5-di-tert-butyl-4-hydroxybenzyl-phosphonate and the calcium salt of monoethyl 3,5-di-tert-butyl-4-hydroxybenzyl-phosphonate.

6. Acylaminophenols

4-Hydroxy-lauroylanilide, 4-hydroxy-stearoylanilide, 2,4-bis-octylmercapto-6-(3,5-di-tert-butyl-4-hydroxyanilino)-s-triazine and octyl N-(3,5-di-tert-butyl-4-hydroxyphenyl)-carbamate.

7. Esters of β-(3,5-di-tert-butyl-4-hydroxyphenyl)-propionic acid with mono- or polyhydric alcohols, for example with methanol, diethylene glycol, octadecanol, triethylene glycol, 1,6-hexanediol, pentaerythritol, neopentylglycol, tris-hydroxyethylisocyanurate, diethylene thioglycol or bis-hydroxyethyl-oxalic acid diamide.

8. Esters of β-(5-tert-butyl-4-hydroxy-3-methylphenyl)-propionic acid with mono- or polyhydric alcohols, for example with methanol, diethylene glycol, octadecanol, triethylene glycol, 1,6-hexanediol, pentaerythritol, neopentylglycol, tris-hydroxyethylisocyanurate, diethylene thioglycol or di-hydroxyethyl-oxalic acid diamide.

9. Amides of β-(3,5-di-tert-butyl-4-hydroxyphenyl)-propionic acid for example N,N'-bis-(3,5-di-tert-butyl-4-hydroxyphenylpropionyl)-hexamethylenediamine, N,N'-bis-(3,5-di-tert-butyl-4-hydroxyphenylpropionyl)-trimethylenediamine and N,N'-bis-(3,5-di-tert-butyl-4-hydroxyphenylpropionyl)-hydrazine.

Examples of aminic antioxidants:

N,N'-Di-isopropyl-p-phenylenediamine, N,N'-di-sec-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethyl-butyl)-N'-phenyl-p-phenylenediamine, N-(1-methyl-heptyl)-N'-phenyl-p-phenylenediamine, N-cyclohexyl-N'-phenyl-p-phenylenediamine, 4-(p-toluene-sulfonamido)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylamino-phenol, 4-nonanoylamino-phenol, 4-dodecanoylamino-phenol, 4-octadecanoylamino-phenol, di-(4-methoxyphenyl)-amine, 2,6-di-tert-butyl-4-dimethylamino-methylphenol, 2,4'-di-amino-diphenylmethane, 4,4'-diamino-diphenylmethane, N,N,N',N'-tetramethyl-4,4'-diamino-diphenylmethane, 1,2-di-[(2-methyl-phenyl)-amino]-ethane, 1.2-di-(phenylamino)-propane, (o-tolyl)-biguanide, di-[4-(1',3'-dimethyl-butyl)phenyl]amine, tert-octylated N-phenyl-1-naphthylamine, a mixture of mono-and dialkylated tert-butyl-/tert-octyldiphenylamines, 2,3-dihydro-3,3-dimethyl-4H-1,4-benzothiazine, phenothiazine and N-allylphenothiazine.

Examples of other antioxidants:

Aliphatic or aromatic phosphites, esters of thiodipropionic acid or of thiodiacetic acid, or salts of dithiocarbamic or dithiophosphoric acid.

Examples of metal deactivators, for example for copper, are: triazoles, benzotriazoles and derivatives thereof, tolutriazoles and derivatives thereof, 2-mercaptobenzothiazole, 2-mercaptobenzotriazole, 2,5-dimercaptobenzotriazole, 2,5-dimercaptobenzothiadiazole, 5,5'-methylenebisbenzotriazole, 4,5,6,7-tetrahydrobenzotriazole, salicylidine-propylenediamine and salicylaminoguanidine and salts thereof.

Examples of rust inhibitors are:

(a) organic acids and their esters, metal salts and anhydrides, for example:

N-oleoyl-sarcosine, sorbitan monooleate, lead naphthenate, alkenylsuccinic acid anhydrides, for example dodecenylsuccinic anhydride, alkenylsuccinic acid part esters and part amides and 4-nonylphenoxyacetic acid.

(b) Nitrogen-containing compounds, for example;
I. Primary, secondary or tertiary aliphatic or cycloaliphatic amines and amine salts of organic and inorganic acids, for example oil-soluble alkylammonium carboxylates.
II. Heterocyclic compounds, for example: substituted imidazolines and oxazolines.

(c) Phosphorus-containing compounds, for example: amine salts of phosphoric acid partial esters or phosphonic acid partial esters and zinc dialkyldithiophosphates.

(d) Sulfur-containing compounds, for example: barium dinonylnaphthalene-sulfonates and calcium petroleum-sulfonates.

Examples of agents which improve the viscosity index are: polyacrylates, polymethacrylates, vinylpyrrolidone/methacrylate copolymers, polyvinylpyrrolidones, polybutenes, olefin copolymers, styrene/acrylate copolymers and polyethers.

Examples of agents which lower the pour point are: polymethacrylate and alkylated naphthalene derivatives.

Examples of dispersants/surfactants are: polybutenylsuccinic acid amides or imides, polybutenylphosphonic acid derivatives and basic magnesium, calcium and barium sulfonates and phenolates.

Examples of antiwear additives are: compounds containing sulfur and/or phosphorus and/or halogen, such as sulfurized vegetable oils, zinc dialkyldithiophosphates, tritolylphosphate, chlorinated paraffins, alkyl and aryl di- and trisulfides, triphenylphosphorothionates, diethanolaminomethyltolyltriazole and di(2-ethylhexyl)aminomethyltolyltriazole.

Lubricant compositions containing the compounds according to the invention can also contain co-lubricating systems, for example of the customary amounts of a solid lubricant from the series comprising graphite, molybdenum disulfide, boron nitride and polytetrafluoroethylene (PTFE).

The present invention accordingly also relates to the use of compounds of the formula (I) as additives for lubricants and hydraulic fluids and advantageously the use of the mixtures of the compounds of the formulae (II) and (III) and the reaction products of the formula (I) formed therefrom as additives for lubricants or hydraulic fluids, it being possible to choose molar mixing ratios of 3:1 to 1:3, advantageously of 3:2 to 2:3 and preferably of 5:4 to 4:5, for the compounds of the formula (II) to the compounds of the formula (III).

On the basis of the possible uses mentioned above for the compounds of the formula (I) according to the invention, the invention also relates to the use of compositions containing a lubricant or a hydraulic fluid and at least one compound of the formula (I), or containing mixtures of the compounds of the formulae (II) and (III) and the reaction products formed therefrom in the form of compounds of the formula (I). Examples of the nature and composition of such fluids are given above.

Finally, the present invention relates to the novel compounds of the formula

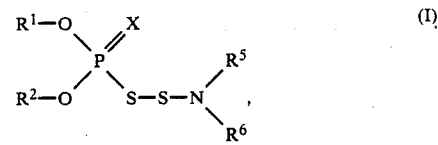

in which $R^1$ and $R^2$ are identical or different and are each an alkyl group having 1 to 30 C atoms, an unsubstituted or $C_1$–$C_8$-alkyl-substituted cycloalkyl group having 5 to 12 C atoms or an unsubstituted or $C_1$–$C_{12}$-alkyl-substituted $C_6$–$C_{10}$-aryl group, or $R^1$ and $R^2$ together are an unsubstituted or $C_1$–$C_{12}$-alkyl-substituted alkylene group having 2 to 10 C atoms or an arylene group having 6 to 20 C atoms, and $R^5$ and $R^6$ are identical or different and are each an alkyl group having 1 to 30 C atoms, or $R^5$ and $R^6$ together are an unsubstituted or $C_1$–$C_{12}$-alkyl-substituted alkylene group having 2 to 20 C atoms or an alkylene group which has 2 to 10 C atoms and is interrupted by —O—, —S— or —$NR^9$—, in which $R^9$ is H or $C_1$–$C_4$-alkyl, and X is O or S, with the proviso that compounds in which $R^1$ and $R^2$ are identical and are an alkyl group having 2, 3 or 4 C atoms and $R^5$ and $R^6$ are identical and are an alkyl group having 2, 3 or 4 C atoms or $R^5$ and $R^6$ together are —$CH_2$—$CH_2$—O—$CH_2$—$CH_2$— or —$(CH_2)_5$— are excluded.

The advantageous compounds include those of the general formula (I) in which $R^1$ and $R^2$ are each a cyclohexyl, phenyl, p-methylphenyl or 2-ethylhexyl group, or $R^1$ and $R^2$ together are a 1-isopropyl-2,2-dimethyltrimethylene, a 2,2-dimethyl-trimethylene, a 2-methyl-2-n-propyl-trimethylene or a 2-methyl-2-n-butyl-trimethylene group, and $R^5$ and $R^6$ are each a 2-ethylhexyl group, or $R^5$ and $R^6$ together with the N atom connecting them are a morpholino group.

The preferred compounds of the formula (I) include:

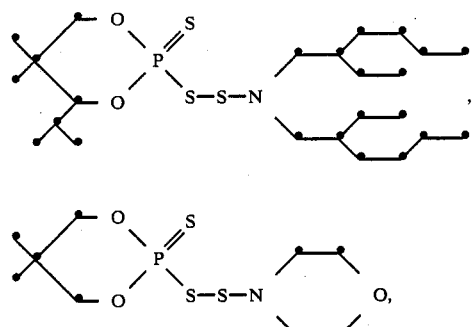

-continued
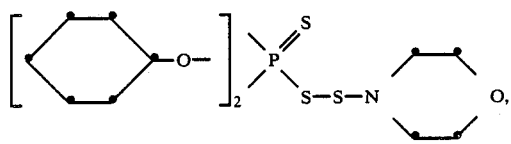
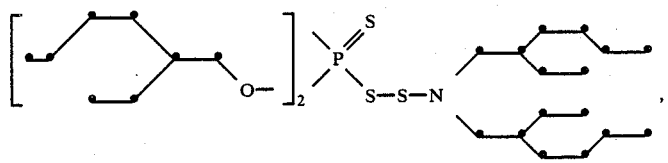
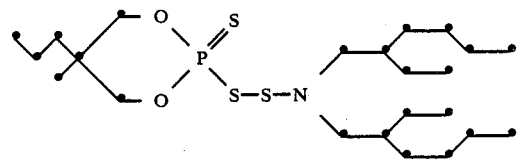
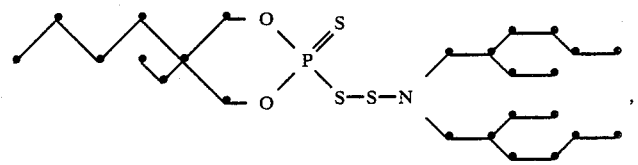
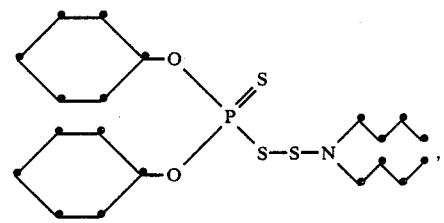
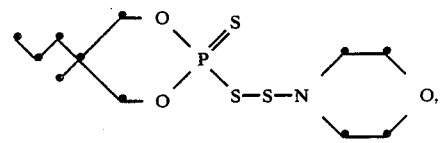
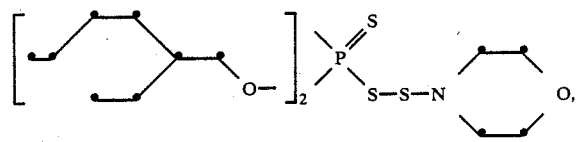
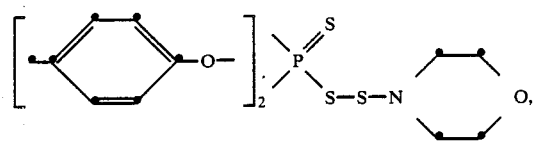
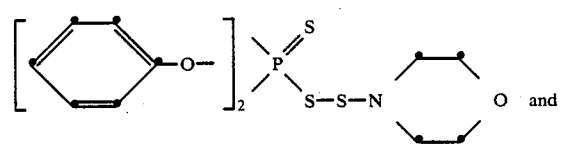

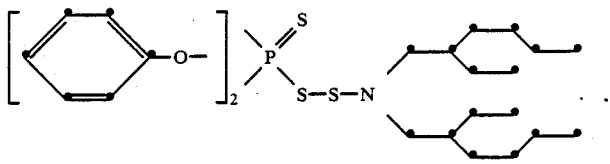

Other groups of compounds and compounds of the formula (I) which are preferred according to the invention can be seen from the preferred compositions defined above.

The following examples illustrate the invention in more detail. In these examples, as in the remainder of the description and in the patent claims, percentages and parts relate to the weight unless indicated otherwise.

PREPARATION EXAMPLE 1

27 parts of bromine are added to 92 parts of bis-(di-2-ethylhexylamino) disulfide in 600 parts of methylene chloride at −20° C. After one hour, 94 parts of potassium 1,3-dioxa-4-isopropyl-5,5-dimethyl-2-phosphorinane-2-thione-2-thiolate, suspended in 500 parts of methylene chloride, are added. The mixture is stirred at −20° C. for one hour and is then warmed to room temperature and stirred for a further 2 hours, and 400 parts of water are added. The organic phase is washed with sodium bicarbonate solution and with water, dried over magnesium sulfate and evaporated. 162 parts of a yellow oil consisting of two components are obtained. 124 parts of pure product are isolated by column chromatography on silica gel (eluting agent: cyclohexane/toluene 3:1), it being possible to allocate the following structure to this product on the basis of its $^{31}$P-NMR signal at 87.8 ppm:

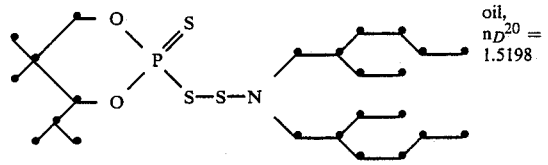

oil, $n_D^{20}$ = 1.5198

| Analysis: | | C | H | N | S |
|---|---|---|---|---|---|
| | calculated | 56.32 | 9.85 | 2.74 | 18.79 |
| | found | 56.54 | 9.84 | 2.74 | 19.07 |

PREPARATION EXAMPLE 2

The following example is particularly good for illustrating this preparation method because of the NMR spectra which are easy to interpret and the good thin layer chromatography separation of all the substances participating in the reaction:

5 parts of bis-(1,3-dioxa-5,5-dimethyl-2-thione-2-phosphorinyl) disulfide and 3 parts of bis-morpholino disulfide are dissolved in 370 parts of toluene and the solution is refluxed, under nitrogen. After 10 hours, the reaction of the educts is already complete; the reaction mixture is further refluxed for another 6 hours and then evaporated and the residue is analyzed by NMR spectroscopy without any purification.

The crude product from this preparation example accordingly contains about 84% of the desired compound of the formula:

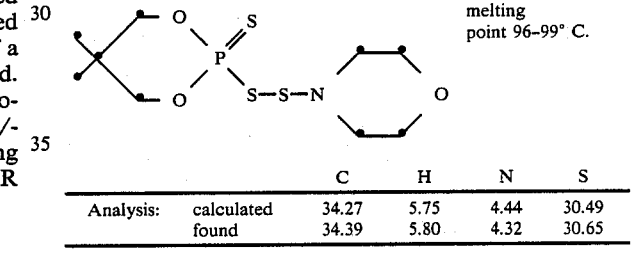

melting point 96–99° C.

| Analysis: | | C | H | N | S |
|---|---|---|---|---|---|
| | calculated | 34.27 | 5.75 | 4.44 | 30.49 |
| | found | 34.39 | 5.80 | 4.32 | 30.65 |

This result is confirmed in the thin layer chromatography (silica gel; toluene/ethyl acetate 19:1).

The following compounds are prepared analogously to Example 1 or Example 2:

3 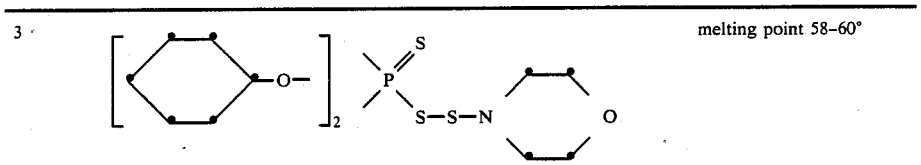

melting point 58–60°

4 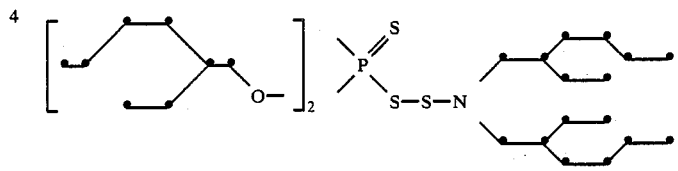

oil $n_D^{20}$ = 1.4978

-continued

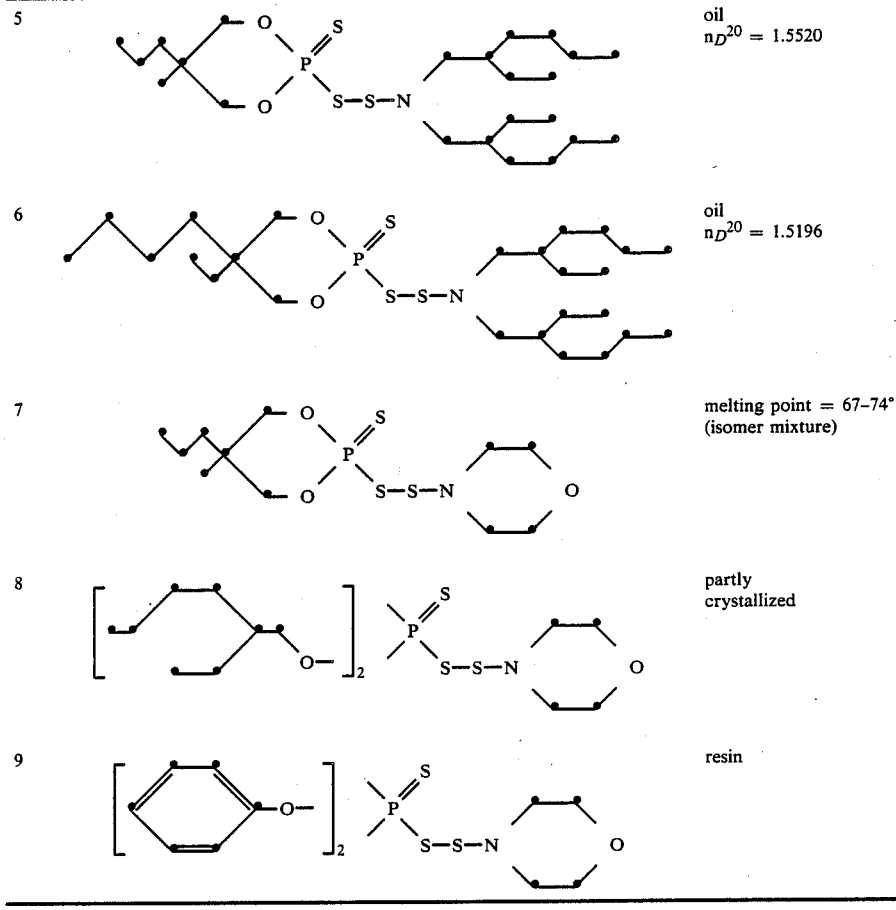

USE EXAMPLE 10

In this example, the temperature at which the substances under investigation reach their maximum rate of decomposition (DTG peak) is determined; the latter is a good measure of the ability of a molecule to decompose in the lubricating oil at the correct moment and to form a wear-preventing reactive layer on the metal to be protected. The decomposition temperature is determined by thermogravimetry by means of a constant heating up rate of 5° per minute; experience shows that values of between 150° and 220° C. here are optimum for most applications. The results are summarized with those of Example 11 in the same table.

USE EXAMPLE 11

The corrosiveness to copper is determined in accordance with ASTM standard method D 130 (3 hours at 120° C.); the results of 1% solutions of the products according to the invention in a basic oil (Catenex®P941 from Shell) and 0.03% of a commercially available copper passivator of the 1-(di-2-ethylhexyl)-aminomethyltolutriazole type are shown in the table.

The evaluation is made in 4 stages:
1-no coating
2-moderate coating
3-severe coating
4-corrosion B represents a fine subdivision between the numerical groups 1 to 4 and means the formation of shadow on the samples. In the qualitative evaluation A to E, the rating A precedes B, B precedes C and so on.

The test for antiwear properties is also carried out. ASTM standard method D-2783-81 using the Shell four ball tester (FBT) is used for testing for suitability as an antiwear additive. Catenex ®P941 from Shell is used as the basic oil. (a) The weld load WL (Weld Load) as the load (in kg) at which the 4 balls weld together within 10 seconds and (b) average wear scar diameter (WSD) under a load of 40 kg over 1 hour (in mm) are determined.

The results of these tests are summarized in the following table.

TABLE

| Additive | DTG-peak | Copper corrosion D 130 | FBT WL | WSD |
|---|---|---|---|---|
| — | | 1B | 1450 | 0.90 |
| Example 1 | 201 | 1B | 2000 | 0.50 |
| Example 3 | 209 | 1B | 2200 | 0.50 |

What is claimed is:
1. A composition comprising:
(a) at least one substrate selected from the group consisting of a lubricant and a hydraulic fluid and
(b) an amount effective to provide high pressure and antiwear action and to reduce corrosion of at least one compound of the formula

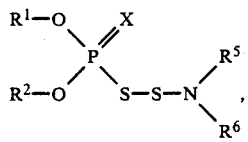

(I)

in which $R^1$ and $R^2$ are identical or different and are each an alkyl group having 1 to 30 C atoms, an unsubstituted or $C_1$–$C_8$-alkyl-substituted cycloalkyl group having 5 to 12 C atoms, or an unsubstituted or $C_1$–$C_{12}$-alkyl-substituted $C_6$–$C_{10}$-aryl group, or $R^1$ and $R^2$ together are an unsubstituted or $C_1$–$C_{12}$-alkyl-substituted alkylene group having 2 to 20 C atoms or an arylene group having 6 to 20 C atoms, and $R^5$ and $R^6$ are identical or different and are each an alkyl group having 1 to 30 C atoms, or $R^5$ and $R^6$ together are an unsubstituted or $C_1$–$C_{12}$-alkyl-substituted alkylene group having 2 to 20 C atoms or an alkylene group which has 2 to 10 C atoms and is interrupted by —O—, —S— or —$NR^9$—, in which $R^9$ is H or $C_1$–$C_4$-alkyl, and X is O or S.

2. A composition according to claim 1, containing at least one compound of the formula (I) formed in situ in the substrate as a reaction product of at least one compound of the formula

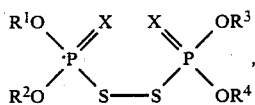

(II)

in which $R^1$ and $R^2$ are as defined in claim 1 and $R^3$ and $R^4$ are identical or different and are as defined in claim 1 for $R^1$ or $R^2$, or $R^3$ and $R^4$ together are as defined in claim 1 for $R^1$ and $R^2$ together, and at least one compound of the formula

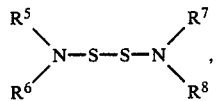

(III)

in which $R^5$ and $R^6$ are as defined in claim 1 and $R^7$ and $R^8$ are identical or different and are as defined for $R^5$ and $R^6$, or $R^7$ and $R^8$ together are as defined in claim 1 for $R^5$ and $R^6$ together.

3. A composition according to claim 2, in which, in the compounds of the formula (II), in each case the substituents $R^1$ and $R^2$ are identical and $R^3$ and $R^4$ are identical, or the substituents $R^1$, $R^2$, $R^3$ and $R^4$ are identical.

4. A composition according to claim 2, in which, in the compounds of the formula (III) in each case the substituents $R^5$ and $R^6$ are identical and $R^7$ and $R^8$ are identical or the substituents $R^5$, $R^6$, $R^7$ and $R^8$ are identical.

5. A composition according to claim 1, in which, in the compounds of the formula (I), the substituents $R^1$ and $R^2$ are identical and are an alkyl group having 5 to 12 C atoms, phenyl, a $C_1$–$C_8$-alkyl-substituted phenyl group or an unsubstituted or $C_1$–$C_4$-alkyl-substituted cycloalkyl group having 6–8 C atoms, or $R^1$ and $R^2$ together are a branched alkylene group having 4–9 C atoms.

6. A composition according to claim 2, in which, in the compounds of the formula (II), the substituents $R^1$ and $R^2$ are identical and are an alkyl group having 5 to 12 C atoms, phenyl, a $C_1$–$C_8$-alkyl-substituted phenyl group or an unsubstituted or $C_1$–$C_4$-alkyl-substituted cycloalkyl group having 6–8 C atoms, or $R^1$ and $R^2$ together are a branched alkylene group having 4–9 C atoms.

7. A composition according to claims 1, in which, in the compounds of the formula (I), the substituents $R^5$ and $R^6$ are identical and are an alkyl group having 5–12 C atoms, or $R^5$ and $R^6$ together are an alkylene group having 4 to 6 C atoms or an alkylene group which has 4 to 6 C atoms and is interrupted by —O—.

8. A composition according to claim 2, in which, in the compounds of the formula (III), the substituents $R^5$ and $R^6$ are identical and are an alkyl group having 5–12 C atoms, or $R^5$ and $R^6$ together are an alkylene group having 4 to 6 C atoms or an alkylene group which has 4 to 6 C atoms and is interrupted by —O—.

9. A composition according to claim 1, in which the substituents $R^5$ and $R^6$ in the formula (I) together with the N atom connecting them are a morpholino group, or $R^5$ and $R^6$ are each a 2-ethyl-hexyl group.

10. A composition according to claim 2, in which the substituents $R^5$ and $R^6$ in the formula (III) together with the N atom connecting them are a morpholino group, or $R^5$ and $R^6$ are each a 2-ethyl-hexyl group.

11. A composition according to claim 1, in which, in the formula (I), X is S.

12. A composition according to claim 2, in which, in the formula (II), X is S.

13. A composition according to claim 1, containing at least one compound of the formula (I) in a concentration of 0.01 to 10% by weight, based on the total composition.

14. A composition according to claim 2, comprising the compounds of the formula (I) and also the compounds of the formula (II) as a result of the use of a molar ratio of II and III of <1:1 to 3:1.

15. A composition according to claim 2, comprising the compounds of the formula (I) and also the compounds of the formula (III) as a result of the use of a molar ratio of III and II of <1:1 to 3:1.

* * * * *